(12) United States Patent
Säll et al.

(10) Patent No.: US 12,115,305 B2
(45) Date of Patent: Oct. 15, 2024

(54) MICRO NOZZLE ASSEMBLY (71) Applicant: SHL MEDICAL AG, Zug (CH)

(72) Inventors: Daniel Säll, Segeltorp (SE); Johan Midbjer, Sturefors (SE); Stefan Gylleby, Akersberga (SE); Thomas Dietl, Falkenfels (DE); Mattias Myrman, Tyreso (SE)

(73) Assignee: SHL Medical AG, Zug (CH)

( * ) Notice: Subject to any disclaimer, the term of this patent is extended or adjusted under 35 U.S.C. 154(b) by 997 days.

(21) Appl. No.: 17/054,922

(22) PCT Filed: May 2, 2019

(86) PCT No.: PCT/EP2019/061297
§ 371 (c)(1),
(2) Date: Nov. 12, 2020

(87) PCT Pub. No.: WO2019/223982
PCT Pub. Date: Nov. 28, 2019

(65) Prior Publication Data
US 2021/0220578 A1    Jul. 22, 2021

(30) Foreign Application Priority Data

May 21, 2018  (EP) .................................... 18173416
Dec. 12, 2018 (EP) .................................... 18212108

(51) Int. Cl.
*A61M 15/00* (2006.01)
*B05B 1/14* (2006.01)
*B05B 15/65* (2018.01)

(52) U.S. Cl.
CPC ........ *A61M 15/009* (2013.01); *A61M 15/002* (2014.02); *A61M 15/0021* (2014.02);
(Continued)

(58) Field of Classification Search
CPC .............. A61M 15/009; A61M 15/002; A61M 15/0021; A61M 15/0065; A61M 15/06;
(Continued)

(56) References Cited

U.S. PATENT DOCUMENTS 3,762,409 A * 10/1973 Lester .................. A61M 11/002
261/78.2
2004/0031485 A1    2/2004 Rustad et al.
(Continued)

FOREIGN PATENT DOCUMENTS

CA         2880592 A1    2/2014
CN         1697708 A    11/2005
(Continued)

OTHER PUBLICATIONS

International Search Report and Written Opinion for Int. App. No. PCT/EP2019/061297, mailed Jul. 24, 2019.

*Primary Examiner* — Kendra D Carter
*Assistant Examiner* — Maap Ahmed Ellabib
(74) *Attorney, Agent, or Firm* — McDonnell Boehnen Hulbert & Berghoff LLP (57) ABSTRACT

A carrier assembly for a spray device, which carrier assembly comprises a carrier member adapted to be mounted in a cartridge adapter of a spray device, which carrier member has a proximally directed first surface, and a through-hole placing the first surface in fluid communication with the second surface; a micro nozzle having an outlet surface, an inlet surface, and a channel placing an inlet orifice at the inlet surface in communication with an outlet orifice at the outlet surface and wherein the micro nozzle is accommodated and attached to the carrier member such that the outlet orifice is aligned with the through-hole, and wherein the carrier member comprises vent holes formed to allow air to flow between the second surface and the first surface.

18 Claims, 8 Drawing Sheets

(52) U.S. Cl.
CPC ............... *B05B 1/14* (2013.01); *B05B 15/65* (2018.02); *A61M 2205/0211* (2013.01); *A61M 2205/0233* (2013.01); *A61M 2205/0238* (2013.01); *A61M 2206/11* (2013.01)

(58) Field of Classification Search
CPC .......... A61M 15/08; A61M 2205/0211; A61M 2205/0233; A61M 2205/0238; A61M 2206/11; A61M 2202/0468; A61M 2207/00; B05B 1/14; B05B 1/65
See application file for complete search history.

(56) References Cited

U.S. PATENT DOCUMENTS

| | | |
|---|---|---|
| 2005/0183718 A1 | 8/2005 | Wuttke et al. |
| 2008/0000470 A1 | 1/2008 | Minocchieri et al. |
| 2010/0154792 A1 | 6/2010 | Geser et al. |
| 2015/0136876 A1 | 5/2015 | Bartels et al. |
| 2017/0281880 A1 | 10/2017 | Van Egmond et al. |

FOREIGN PATENT DOCUMENTS

| | | |
|---|---|---|
| CN | 101104463 A | 1/2008 |
| CN | 101247897 A | 8/2008 |
| CN | 203091186 U | 7/2013 |
| CN | 106573134 A | 4/2017 |
| JP | S57-119756 | 7/1982 |
| JP | 2015-528745 A | 10/2015 |
| WO | 02/098666 A1 | 12/2002 |
| WO | 2008/151796 A2 | 12/2008 |
| WO | 2012/092163 A1 | 7/2012 |

\* cited by examiner

MICRO NOZZLE ASSEMBLY

CROSS REFERENCE TO RELATED APPLICATIONS

The present application is a U.S. National Phase Application pursuant to 35 U.S.C. § 371 of International Application No. PCT/EP2019/061297 filed May 2, 2019, which claims priority to European Patent Application No. 18173416.1 filed May 21, 2018 and European Patent Application No. 18212108.7, filed Dec. 12, 2018. The entire disclosure contents of these applications are herewith incorporated by reference into the present application.

TECHNICAL AREA

The present disclosure relates to a micro nozzle assembly, and in particular to a micro nozzle assembled with a carrier member.

BACKGROUND

There are many different kinds of spray devices on the market today. Micro nozzle devices comprising micro nozzles form an increasingly important and growing segment of the market. Micro nozzles may for instance be found in ink jet printing appliances, 3D printers, perfume containers and medicament delivery devices. Such nozzles comprise orifices for expelling the liquid spray, which orifices have diameters between 0.5 µm and 10 µm. To produce nozzles in the lower diameter range, the small dimensions require the orifices to be produced in micro technology processes, such as by etching channels in a semiconductor wafer, which wafer is thereafter diced into individual nozzles. In order to increase the yield of each wafer, the nozzle dies are preferred to be made as small as possible, each typically having a surface area of 1 mm$^2$ or even smaller. Obviously, problems are encountered when such small components are to be assembled with the spray device. In particular, the orifices must not become damaged or obstructed during handling, such as assembly with other parts of the spray device.

US2017281880 discloses a method of mounting micro nozzle dies in a thermoplastic holder. The die is heated to thermally deform the plastic of the holder as the die is pushed into position. After the die and the plastic cool, the die is firmly mounted in the holder. However, it is difficult to position the die in the holder with a high degree of precision. In addition, the assembly of the die and the holder results in a depression at an outlet surface of the nozzle, where the thermoplastic holder forms the side walls of the depression. When the nozzle is in use, residual spray liquid may accumulate in the depression and cause clogging of the orifices, and may increase the risk of ingrowth of bacteria through the nozzle into the liquid reservoir on the other side of the nozzle, which is particularly disadvantageous when the liquid reservoir is the primary medicament container of a medicament delivery device, e.g. an inhalation device.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

In view of the background discussion, a general object of the present disclosure is to provide carrier assembly where a micro nozzle is assembled with a carrier member such that the assembly may be conveniently handled for assembly with a spray device. A further general object of the present disclosure is to provide a carrier assembly where a residual spray liquid at an outlet surface of the nozzle may escape, or be easily cleaned out.

According to a main aspect of the disclosure it is characterised by a carrier assembly for a spray device, which carrier assembly comprises a carrier member adapted to be mounted in a dispenser unit of a spray device, which carrier member has a proximally directed first surface, a distally directed second surface, and a through-hole placing the first surface in communication with the second surface; a micro nozzle having an outlet surface, an inlet surface, and a microchannel placing an outlet orifice of the outlet surface in communication with an inlet orifice of the inlet surface; and wherein the micro nozzle is accommodated and attached to the carrier member such that the outlet orifice is aligned with the through-hole, and wherein the carrier member comprises vent holes formed to allow air to flow between the second surface and the first surface.

As such, the attachment of the micro nozzle to the carrier member allows easier handling of the micro nozzle as compared to handling the micro nozzle on its own, without a carrier member. Furthermore, the vent holes allow air to flow, such as to shape an airflow around the outlet orifice of the micro nozzle. This is particularly advantageous in inhalation applications, where the airflow may be used to prevent droplets of a sprayed aerosol from depositing on surfaces of the cartridge adapter. The airflow may be generated by inhalation of a user of the cartridge adapter.

According to another aspect of the disclosure the carrier member is formed out of thin sheet metal, such as steel, such as from a metal strip of steel.

According to another aspect of the disclosure the vent holes are arranged around the through-hole (66), such as in a circular or semi-circular pattern.

According to another aspect of the disclosure the diameters of the vent holes are between 0.05 mm and 0.3 mm, or more preferably between 0.1 and 0.17 mm.

According to another aspect of the disclosure the through-hole of the carrier member is configured to accommodate the micro nozzle such that the outlet surface of the micro nozzle is flush with the first surface, or raised relative to the first surface, of the carrier member when the micro nozzle is accommodated in the through-hole.

Allowing the outlet surface of the micro nozzle to protrude from, or be flush with, the first surface of the carrier member provides a convenient structure for wiping liquid off the surface, or for liquid to run off the surface spontaneously, such as if the surfaces are made hydrophobic.

According to another aspect of the disclosure the micro nozzle further comprises an inlet surface generally parallel with the outlet surface, and a side surface profile connecting the outlet surface with the inlet surface, and wherein the side surface profile is configured to cooperate with the through-hole such that the outlet surface is flush with the first surface, or raised relative to the first surface, when the micro nozzle is accommodated in the through-hole.

The shape of the through-hole cooperates with the shape of the side surface of the micro nozzle such that assembly of the two components immediately results in the outlet surface protruding above the first surface, or being flush with the first surface.

According to another aspect of the disclosure the side surface profile cooperates with the through-hole by abutment with an inside surface profile of the through-hole such that the outlet surface is flush with the first surface, or raised relative to the first surface, when the micro nozzle is accommodated in the through-hole.

It is the abutment of the two side surface profiles that provide a stop for determining the position of the micro nozzle in relation to the carrier member.

According to another aspect of the disclosure the side surface profile of the micro nozzle is angled relative to the outlet surface and wherein the inside surface profile of the through-hole of the carrier member is correspondingly angled relative to the first surface to provide a firm accommodation of the micro nozzle in the through hole.

Corresponding angles of the side surface profile and the inside surface profile provide a stable seat which may accommodates the micro nozzle in the through-hole.

According to another aspect of the disclosure the inside surface profile of the through-hole is an angled surface formed by punching from the second surface to the first surface.

The angled surface of the inside surface of the carrier member may be created simply by punching a through-hole in the carrier member, where the side walls of the through-hole protrude from the first surface at an angle, wherein the angle on the inside of the through-hole is configured to correspond to the angle of the side surface profile of the micro nozzle.

According to another aspect of the disclosure the side surface profile of the micro nozzle is stepped such as to provide an intermediate, proximally-facing surface between the inlet surface and the outlet surface.

An alternative to the angled side surface is to provide a stepped side surface profile of the micro nozzle. The intermediate surface is thus generally parallel with both the inlet surface and the outlet surface.

According to another aspect of the disclosure the side surface profile of the micro nozzle is stepped such that the intermediate surface of the micro nozzle abuts a distally-facing surface of the inside surface profile of the through-hole, when the micro nozzle is accommodated in the through-hole.

The abutment of the intermediate surface with the distally-facing surface of the through-hole thus determines the position of the micro nozzle in relation to the carrier member.

According to another aspect of the disclosure the micro nozzle comprises a ceramic or a monocrystalline material, such as a semiconductor.

In order to provide the small dimensions by micromachining and/or semiconductor processing, the material of the micro nozzle has to be carefully chosen.

According to another aspect of the disclosure the side surface profile of the micro nozzle is formed by laser dicing, such as stealth dicing.

Laser dicing allows a method of forming and separating the micro nozzles from a wafer, which method is substantially free from particles which could otherwise clog the orifices of the micro nozzles.

According to another aspect of the disclosure the side surface profile of the micro nozzle is formed by cutting and/or milling, such as dicing and/or grinding.

A mechanical cutting method is possible but not preferable due to the high risk of clogging the orifices with saw dust and particles.

According to another main aspect of the disclosure it is characterised by spray device comprising the carrier assembly according to any of the foregoing aspects.

According to another aspect of the disclosure the spray device is a medicament delivery device, such as an inhalation device or an eye spray device.

According to another aspect of the disclosure the spray device is a perfume dispenser.

These and other aspects of, and advantages with, the present disclosure will become apparent from the following detailed description of the present disclosure and from the accompanying drawings.

BRIEF DESCRIPTION OF DRAWINGS

In the following detailed description of the present disclosure, reference will be made to the accompanying drawings, of which

DETAILED DESCRIPTION

Figure 1:
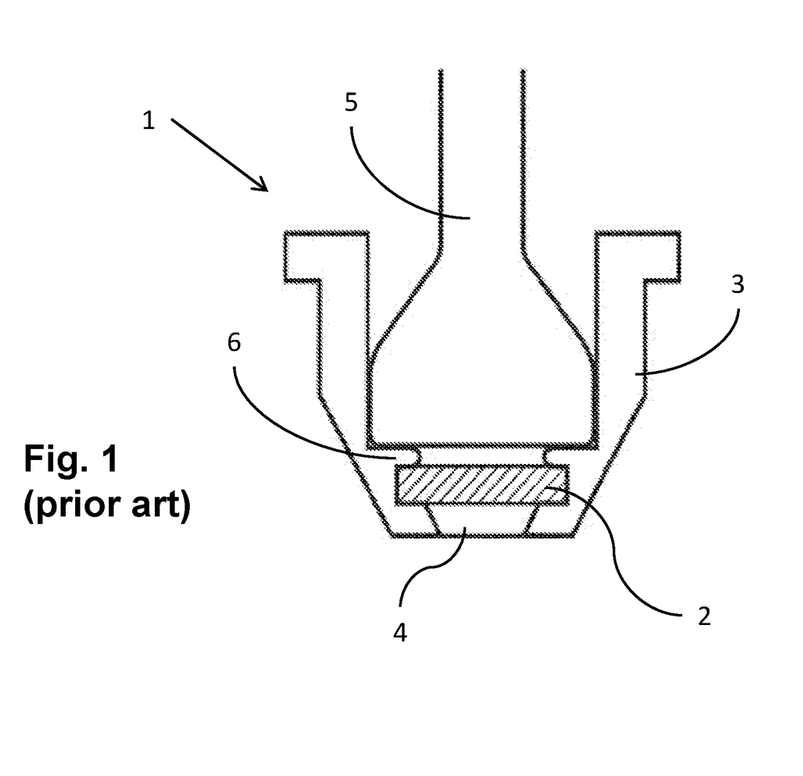
FIG. 1 shows a perspective view of a prior art assembly method

A cross section view of a prior art micro nozzle assembly 1 is shown in FIG. 1. A micro nozzle 2 has been heated and pushed into a tapered seat of a thermoplastic holder 3. FIG. 1 shows the subsequent step where a thermode 5 is pressed into the seat behind the nozzle to create a rivet-like flange 6 of the thermoplastic material, which further secures the micro nozzle in the seat. As can be seen, a depression 4, or cavity, is formed in the holder 3 in front of the nozzle 2. Such a depression may accumulate spray liquid, which may dry, or solidify, and may clog orifices of the micro nozzle 2. The accuracy of the positioning of the micro nozzle 2 in the holder according to this method is further unsatisfactory. It is an object of the present disclosure to improve on these issues.

Figure 2A:
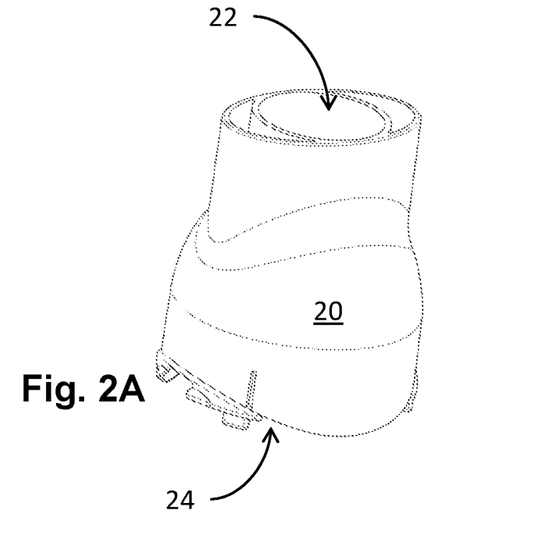
FIG. 2A shows a perspective view of a dispenser unit of a spray device

FIG. 2A shows a perspective view of an exemplary embodiment of a dispenser unit 20 of a spray device. A micro nozzle 50 (FIG. 2B) is mounted in the dispenser unit. The dispenser unit 20 has proximal side 22, through which an aerosol is sprayed, and a distal side 24 which is mounted on a spray device. In this exemplary embodiment, the dispenser unit 20 is a mouthpiece of an inhalation spray device, but many other types of dispenser units, for any applications requiring a very fine aerosol, are conceivable. Other examples include eye spray devices and perfume dispensers, to name but a few.

A micro nozzle is herein defined as a nozzle having orifice diameters between 0.5 µm and 10 µm, which may produce an aerosol of very fine droplets by pressurising a liquid on an inlet side 54 of the nozzle, which liquid is expelled as droplets at an outlet side 52 of the nozzle. Droplet diameters may be approximately 1 µm in the lower range of orifice diameters. Depending on viscosity, pressure and orifice diameters, the expelled liquid may form into Rayleigh droplet trains. A micro nozzle has at least one orifice on the inlet side and at least one orifice on the outlet side, which inlet and outlet orifices are connected inside the micro nozzle by cavities and/or channels. The channels and orifices are not essential in themselves for this disclosure. However, as shown in FIG. 2C, it is customary to provide a larger number of orifices on the inlet side 54 than on the outlet side 52 because the orifices are normally formed in membranes which cover a cavity, or channel, in the micro nozzle. It is therefore preferable have a smaller pressure drop on the inlet side 54 than on the outlet side 52. In FIG. 2C, the orifices are symbolised by areas of dark dots. Outlet orifices 57 are shown on the proximal outlet side 52 and inlet orifices 59 are shown on the distal inlet side 54. The micro nozzle 50 comprises a ceramic or a monocrystalline material, such as a semiconductor material, which is suitable for micro structure processing.

Figure 2B:
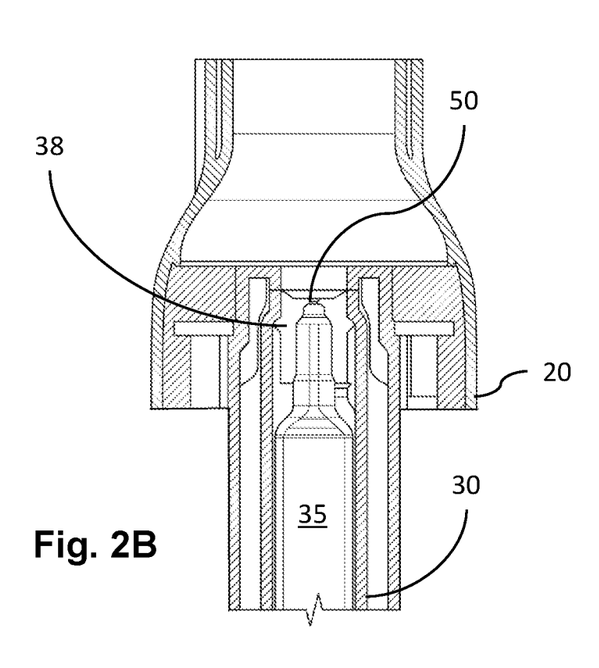
FIG. 2B shows a cross-sectional view of a micro nozzle assembled with a dispenser unit and a container for spray liquid
Figure 2C:
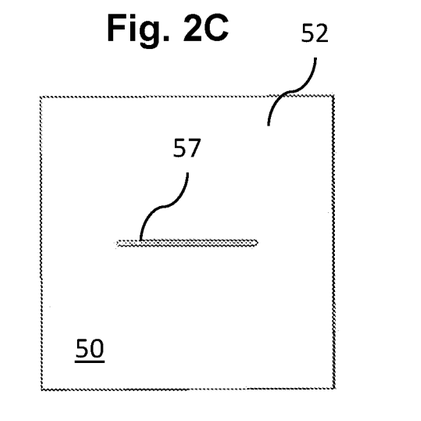
FIG. 2C shows a conceptual view of a proximally facing outlet side of a micro nozzle
Figure 2D:
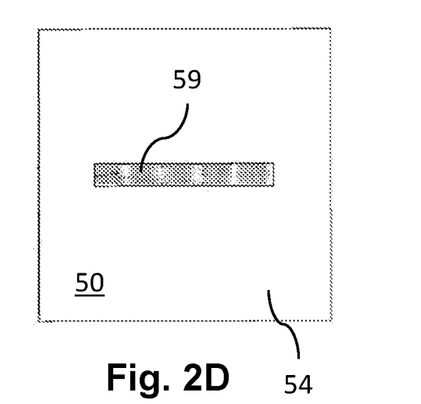
FIG. 2D shows a conceptual view of a distally facing inlet side of a micro nozzle

FIG. 2B shows a cross-sectional view of the dispenser unit 20 of FIG. 2A, where a container holder 30, comprising a container 35, is connected to the dispenser unit 20. The container 35 holds a liquid which is to be pressurised and pushed through the micro nozzle 50 to form an aerosol. A thermoplastic cartridge adapter 38 is arranged to hold the micro nozzle 50 in position relative to the container 35 and the dispenser unit 20. In FIG. 2B, the micro nozzle 50 is mounted in the cartridge adapter 38 according to the prior art exemplary method of FIG. 1.

Figure 3A:
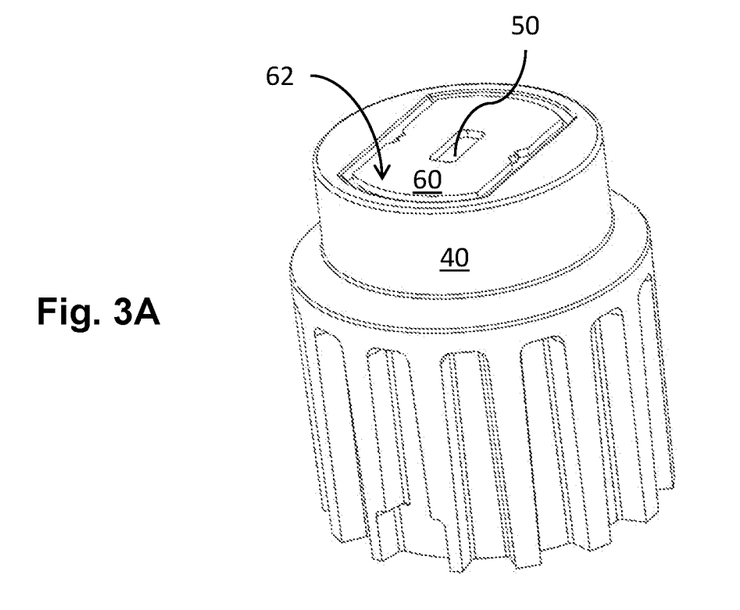
FIG. 3A shows a perspective view of a cartridge adapter comprising a carrier assembly according to the present disclosure
Figure 3B:
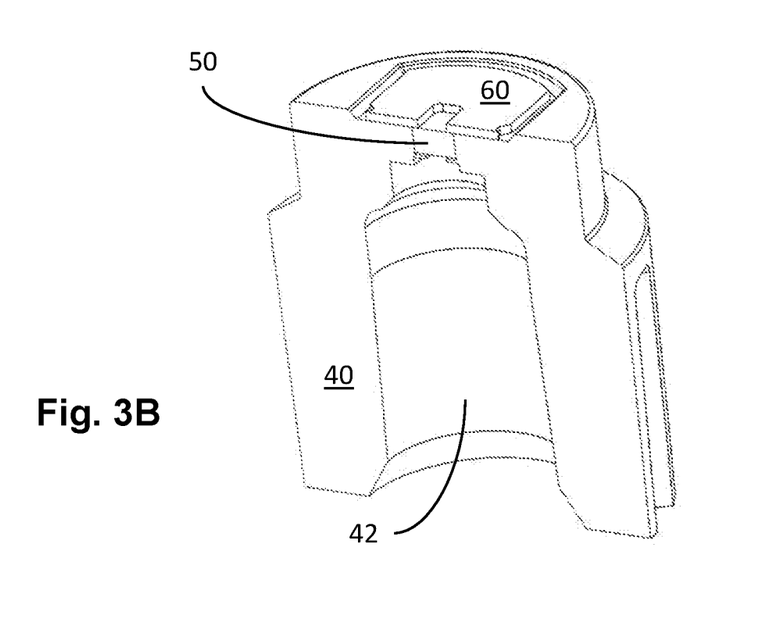
FIG. 3B shows a perspective cross-sectional view of a cartridge adapter comprising a carrier assembly according to an embodiment of the present disclosure
Figure 3C:
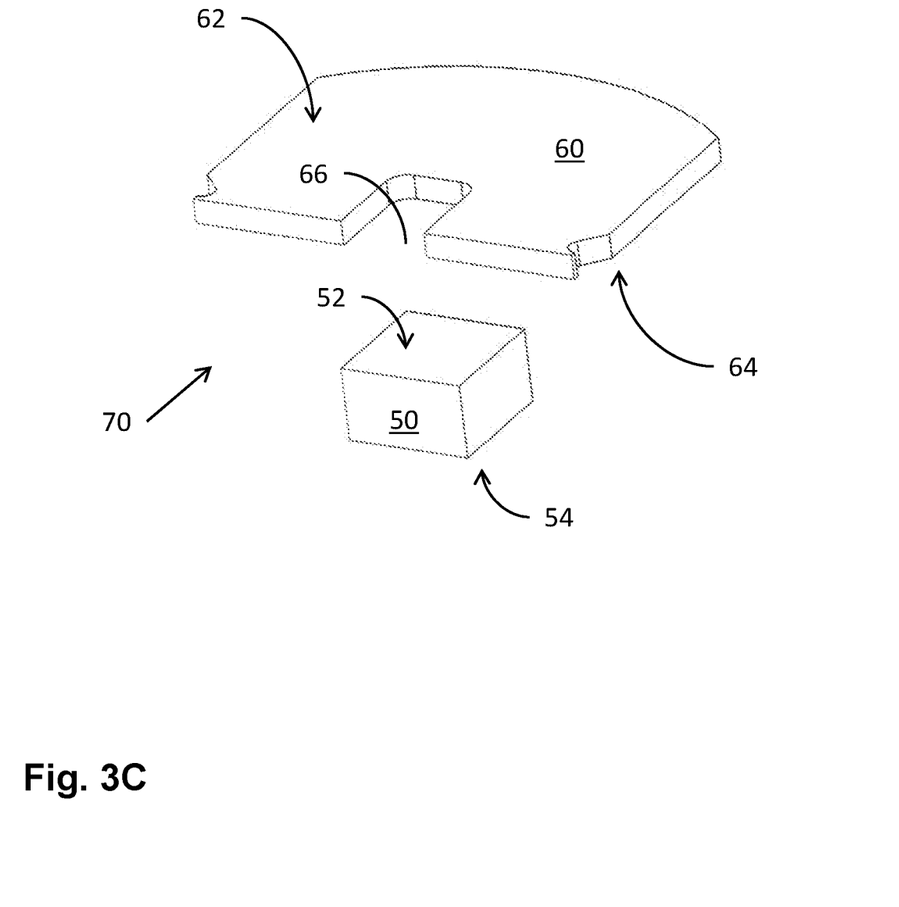
FIG. 3C shows a perspective cross-sectional view of a carrier assembly according to an embodiment of the present disclosure
Figure 4A:
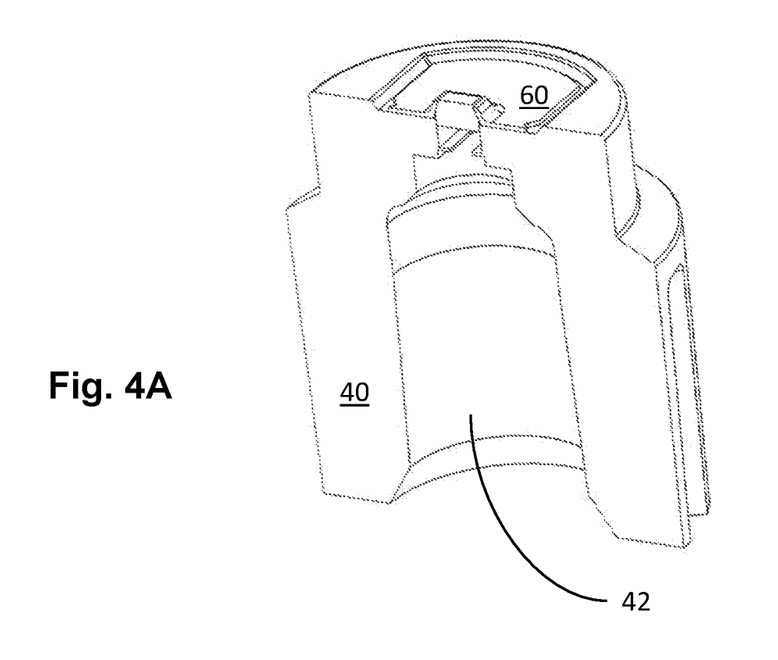
FIG. 4A shows a perspective cross-sectional view of a cartridge adapter comprising a carrier assembly according to an embodiment of the present disclosure
Figure 4B:
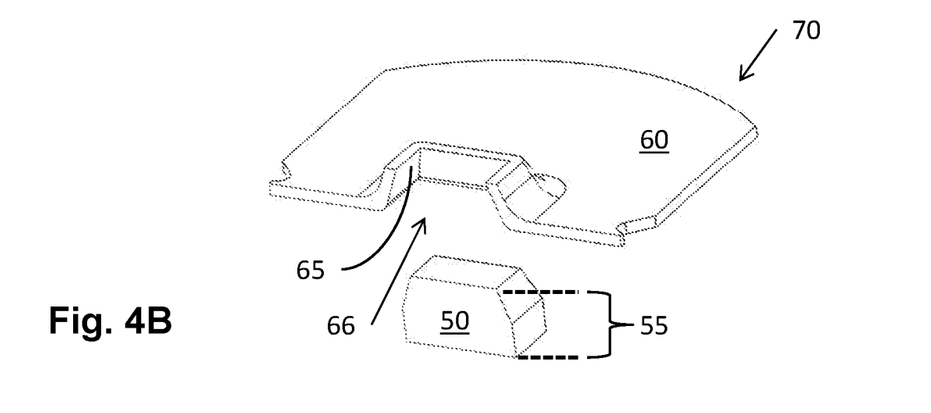
FIG. 4B shows a perspective cross-sectional view of a carrier assembly according to an embodiment of the present disclosure
Figure 4C:
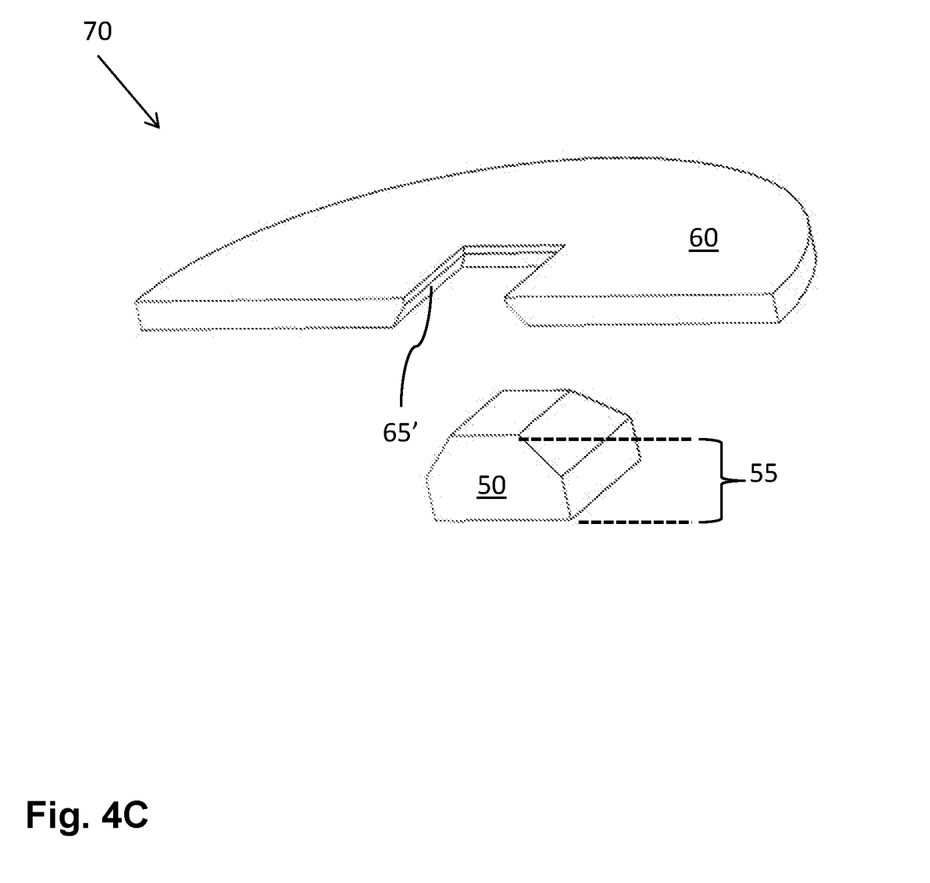
FIG. 4C shows a perspective cross-sectional view of a carrier assembly according to an embodiment of the present disclosure
Figure 5A:
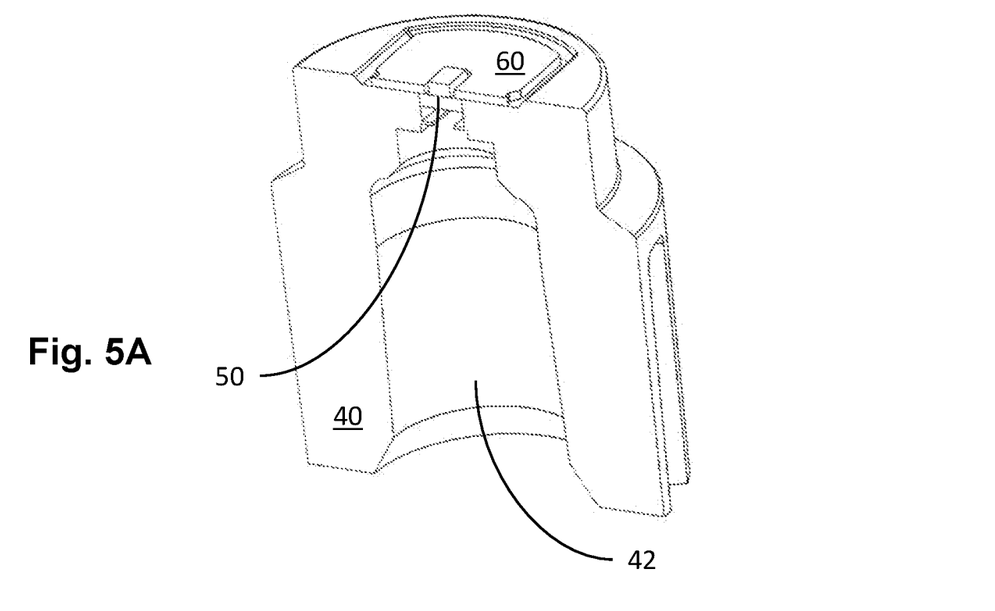
FIG. 5A shows a perspective cross-sectional view of a cartridge adapter comprising a carrier assembly according to an embodiment of the present disclosure
Figure 5B:
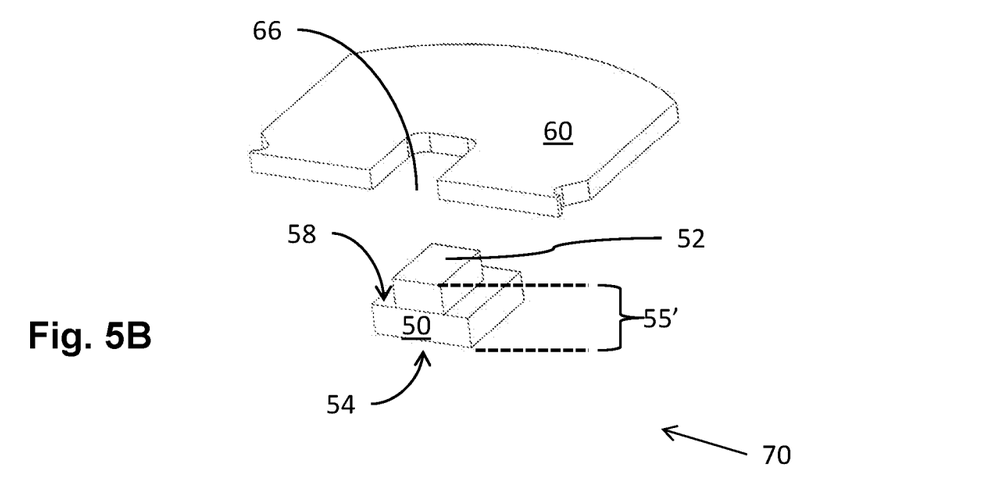
FIG. 5B shows a perspective cross-sectional view of a carrier assembly according to an embodiment of the present disclosure

FIGS. 3A-3C shows a first embodiment of the present disclosure. The cartridge adapters 40; 40' (see FIGS. 6A and 6B) of the exemplary embodiments of this disclosure are adapted to receive a carrier member 60 which in turn accommodates the micro nozzle 50, i.e. a carrier assembly 70 (FIG. 3C). The cartridge adapter 40 further comprises a seat 42 for a proximal end of the container 35 such that a pressurised liquid of the container 35 may be expelled through the micro nozzle 50. The cartridge adapter 40; 40' is generally defined as a component which comprises the carrier assembly 70, which component may be directly connected to a primary package, e.g. a syringe, a cartridge or any other liquid container which may be pressurised. Such a component may alternatively be connected to a metered dose chamber, where a liquid to be sprayed may also be pressurised and pushed through the micro nozzle 50 to form the aerosol. The term cartridge adapter may include an aerosol unit, or mix chamber, where a sprayed liquid is mixed with air to form the aerosol, in so far as the aerosol unit or mix chamber may be directly connected to the liquid container or chamber.

The carrier assembly 70 thus comprises the carrier member 60 adapted to be mounted in the cartridge adapter 40 of a spray device (not shown), which carrier member 60 has a proximally directed first surface 62, a distally directed second surface 64 (FIG. 3C), and a through-hole 66 (FIG. 3C) placing the first surface 62 in communication with the second surface 64. The micro nozzle 50 of the carrier assembly 70 has an outlet surface 52, an inlet surface 54, and a channel placing an inlet orifice at the inlet surface in communication with an outlet orifice at the outlet surface (not shown). The micro nozzle 50 is accommodated and attached to the carrier member 60 such that the outlet surface 52 is aligned with the through-hole 66. The attachment may be achieved by gluing, soldering or any other method known in the art.

The carrier member 60 may have many different shapes that allow easy handling and assembly with other components. For instance, the carrier member 60 may be produced from a sheet or a roll, e.g. of metal, comprising multiple carrier members 60. The individual components may then be conveniently picked and placed from the sheet or roll by conventional methods. In the exemplary embodiment the carrier member 60 is simply depicted as a plate having planar first and second surfaces. The carrier member 60 may be configured to be glued to the cartridge adapter 40 after receiving the micro nozzle 50. The carrier member 60 may alternatively comprise attachment members which may connect with corresponding attachment members of the cartridge adapter 40.

According to this embodiment, the outlet surface 52 of the micro nozzle 50 is attached to the second surface 64 of the carrier member 60 such that a part of the outlet surface 52, comprising an outlet orifice, is aligned with the through-hole 66. The positioning of the nozzle in relation to the carrier member 60 may thus be precise and the carrier assembly 70 is easy to handle when the micro nozzle 50 is securely accommodated by the carrier member 60. As a consequence, the nozzle will also be precisely positioned in relation to a cartridge 35 and in relation to a dispenser unit 20 when the carrier assembly is mounted in the cartridge adapter 40 in a spray device.

In a preferred embodiment, shown in FIGS. 4 and 5, the through-hole 66 of the carrier member 60 is configured to accommodate the micro nozzle 50 such that the outlet surface 52 of the micro nozzle 50 is flush with the first surface 62, or raised relative to the first surface 62, of the carrier member 60 when the micro nozzle 50 is accommodated in the through-hole 66.

In addition to the advantages described above, the flush or raised surface of the micro nozzle 50, in relation to the carrier member 60, allows for easy removal of any liquid remaining on the outlet surface 52 of the micro nozzle 50 after use, such as by suction or blowing, e.g. an added air flow, or by drying with a sponge or an absorbent. The outlet surface 52 of the micro nozzle 50 and/or the first surface 62 of the carrier member 60 may further be provided with a hydrophobic treatment. Treatments may for instance be a hydrophobic coating or a hydrophobic surface structure, such as conventionally applied in the art. A hydrophobic surface causes remaining liquid droplets to roll off the micro nozzle 50 spontaneously.

The inlet surface 54 of the micro nozzle is further generally parallel with the outlet surface 52. A side surface profile 55 (FIG. 4B connects the outlet surface with the inlet surface. The side surfaces of the micro nozzle 50, between the inlet side and the outlet side, may be shaped to have a cross-sectional profile which may be used in the assembly of the micro nozzle with the carrier member 60. The side surface profile is configured to cooperate with the through-hole 66 such that the outlet surface is flush with the first surface 62, or raised relative to the first surface 62, when the micro nozzle 50 is accommodated in the through-hole 66.

The side surface profiles of the micro nozzles of this disclosure are preferably formed by laser dicing, such as stealth dicing. This method allows precise dicing of a wafer, i.e. cutting the wafer into micro nozzles (nozzle dies), without generating saw dust or other particles which could obstruct the orifices. A less preferable method is to use purely mechanical cutting and/or milling, such as by using a saw blade. Alternatively, the side surface profile may be created by etching the wafer vertically, e.g. anisotropically.

In an embodiment of the present disclosure the side surface profile 55 cooperates with the through-hole by abutment with an inside surface profile 65 of the through-hole 66 such that the outlet surface 52 is flush with the first surface 62, or raised relative to the first surface 62, when the micro nozzle 52 is accommodated in the through-hole 66.

The abutment between the side surface profile 55 of the micro nozzle and the inside surface profile 65 of the through-hole 66 serves as a stop which determines the position of the micro nozzle 55 in relation to the carrier member 65. It is therefore easy and convenient to assemble the micro nozzle 50 and the carrier member 60. The nozzle 50 is also firmly accommodated in the through-hole 60.

FIGS. 4A-4C display two embodiments of the carrier assembly 70, where the side surface profile 55 of the micro nozzle 50 is angled, or at least partly angled, relative to the outlet surface 52 and wherein the inside surface profile 65, 65' of the through-hole 66 of the carrier member 60 is correspondingly angled relative to the first surface 62 to provide a firm accommodation of the micro nozzle 50 in the through hole 66.

In FIG. 4B the inside surface profile 65 of the through-hole 66 is an angled surface formed by punching a hole from the second surface 64 to the first surface 62 of the carrier member 60. After punching, edges of the through-hole 66 are polished, e.g. electropolished, before receiving the micro nozzle 50.

FIG. 4C shows an alternative embodiment where the inside surface profile 65' of the through-hole 66 is angled from the second side 64 to the carrier member 60 to the first side 62 such that an area of the through-hole 66 is larger at the second side 64 than at the first side 62. An area of the inlet surface 54 is larger than the area of the through-hole 66 at the first surface 62, such that it is ensured that the micro nozzle 50 cannot pass through the through-hole 66.

In an alternative embodiment, shown in FIGS. 5A and 5B, the side surface profile 55' of the micro nozzle is stepped such as to provide an intermediate, proximally-facing surface 58 between the inlet surface 54 and the outlet surface 52. The intermediate surface 58 of the micro nozzle abuts a distally-facing surface of the inside surface profile of the through-hole (not shown), when the micro nozzle is accommodated in the through-hole. Alternatively, the intermediate surface 58 may abut the second surface 64. An area of the intermediate surface 58 is larger than the area of the outlet surface 52. The area of the intermediate surface is also larger than the area of the through-hole 66 at the first surface 62, such that it is ensured that the micro nozzle 50 cannot pass through the through-hole 66.

FIGS. 6A and 6B show an additional embodiment of the carrier assembly, which may be applied in combination with the previously described embodiments. FIG. 6A illustrates a perspective cross-sectional view of a cartridge adapter 40', such as an aerosol unit for an inhalation device. FIG. 6B further shows a detailed view of the carrier assembly 70 comprising the carrier member 60 and the micro nozzle 50. As exemplified, the cartridge adapter 40' may be generally tubular. The cartridge adapter 40' may be generally hollow in the axial direction, having an axial fluid flow passage. A distal inlet part may comprise a first tubular part and a proximal outlet part may comprise a second tubular part. The inlet part and the outlet part may be generally coaxially aligned. The second tubular part may have a larger inner diameter than an outer diameter of the first tubular part.

The carrier member 60 may be generally disk-shaped and may be transversally arranged between the first tubular part and the second tubular part. Vent holes 68 of the carrier member 60 may be arranged around the through-hole 66, such as in a circular or semi-circular pattern, wherein an inner diameter of the circular or semi-circular pattern is larger than the outer diameter of the first tubular part, and an outer diameter of the circular pattern is smaller than the inner diameter of the second tubular part.

The carrier member 60 comprises the through-hole 66. The micro nozzle 50 is mounted on the carrier member 60. The micro nozzle 50 covers the through-hole 66. As described above, the micro nozzle 50 is arranged with orifices such that a pressurised fluid may be expelled through the micro nozzle 50, and through the through-hole 66, in the form of a spray. Depending on the pressure and viscosity of the fluid, and on the dimensions of the orifices, the expelled fluid may form Rayleigh droplet trains at the through-hole 66 on the proximal side of the carrier member 60. For Rayleigh droplet train formation of the spray, the orifices may have diameters of 0.5-10 μm and the pressure of the fluid may be 2-60 bars.

The cartridge adapter 40' may comprise a second opening 44' which is aligned and adjacent with the through-hole 66 of the carrier member 60. The second opening 44' may accommodate the micro nozzle 50 by insert-moulding such that a flow passage is formed from the inlet part, through the second opening 44', the orifices of the micro nozzle 35 and the through-hole 66, to the outlet part. The cartridge adapter 40' hermetically seals the micro nozzle 50 and the nozzle carrier 60 to the cartridge adapter 40'. The inlet part of the cartridge adapter 40' may thus be attached to a chamber containing the fluid for spraying, whereby the fluid may be pressurised and expelled from the inlet part into the outlet part.

Preferably, the carrier member 60 is formed out of thin sheet metal, e.g. steel, such as from a metal strip of steel. A metal sheet member allows accurate creation of the vent holes 68 in the carrier member 60, such as by etching. Any additional configuration of shapes or structural features of the carrier member 60 are also simple to create, which structural features facilitate the integration of the carrier assembly in the cartridge adapter 40'.

The carrier member 60 in the form of a metal strip having vent holes, is easily produced and may be conveniently cut from a piece of sheet metal and assembled with a micro nozzle before placing the carrier member, comprising the micro nozzle, in a cartridge adapter moulding tool for insert-moulding. Such vent holes of a metal strip may be accurately and precisely dimensioned and laid out, in contrast to holes of a plastic component, which would suffer from large tolerance variations. In addition, it is difficult to create vent holes having diameters smaller than 0.5 mm in a plastic moulding process.

The size and amount of the vent holes 68 of the carrier member 60, and their layout, may be adapted to determine flow characteristics of airflow in an inhalation device. The size, amount and layout of the vent holes 68 affect a laminar flow, a flow under the coanda effect in the cartridge adapter, and regulates a general resistance of the airflow. In one embodiment, the vent holes 68 have diameters varying between of 0.1 mm and 0.17 mm. The c-c distance may be 0.24 mm. However, it is conceivable to have diameters ranging between 0.05 mm and 0.3 mm. The c-c distance could be 0.1 for smaller diameters.

An important aspect of the vent holes 68, as mentioned above, is to provide an appropriate flow resistance, for instance so that a user of an inhalation device comprising the carrier assembly, in one dose spraying action, draws in a suitable amount of air via the vent holes 68 when operating the device.

Figure 6A:
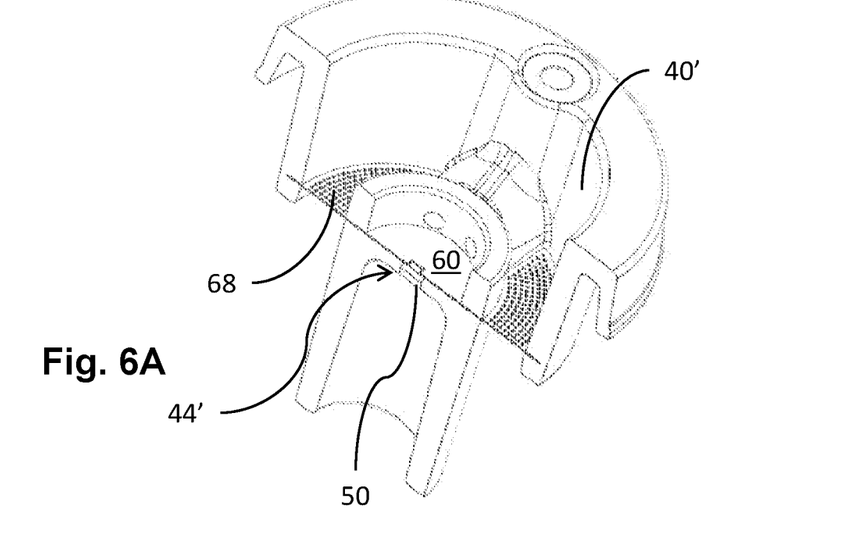
FIG. 6A shows a perspective cross-sectional view of a carrier assembly insert-moulded into an alternative cartridge adapter
Figure 6B:
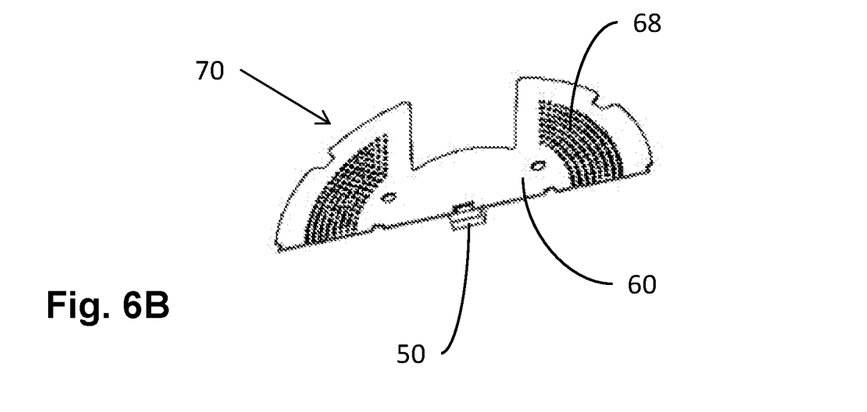
FIG. 6B shows a perspective cross-sectional view of the carrier assembly of FIG. 6A.

The embodiment illustrated in FIGS. 6A and 6B shows an carrier assembly 70 insert-moulded into the cartridge adapter 40', but the carrier assembly 70 wherein the carrier member 60 comprises a micro nozzle 50 as well as vent holes 68 does not require insert-moulding in order to provide the advantages of the vent-holes 68. Accordingly, there is provided a carrier assembly 70 for a spray device, which carrier assembly 70 comprises a carrier member 60 adapted to be mounted in a cartridge adapter 40; 40' of a spray device, which carrier member 60 has a proximally directed first surface 62, a distally directed second surface 64, and a through-hole 66 placing the first surface 62 in fluid communication with the second surface 64; a micro nozzle 50 having an outlet surface 52, an inlet surface 54, and a channel placing an inlet orifice 59 at the inlet surface 54 in communication with an outlet orifice 57 at the outlet surface 52; wherein the micro nozzle 50 is accommodated and attached to the carrier member 60 such that the outlet orifice is aligned with the through-hole, and wherein the carrier member 66 comprises vent holes 68 formed to allow air to flow between the second surface and the first surface.

The invention claimed is:

1. A carrier assembly for a spray device, wherein the carrier assembly comprises a carrier member adapted to be mounted in a cartridge adapter of a spray device, which carrier member has a proximally directed first surface, a distally directed second surface, and a through-hole placing the first surface in fluid communication with the second surface;

a micro nozzle having an outlet surface, an inlet surface, and a channel placing an inlet orifice at the inlet surface in communication with an outlet orifice at the outlet surface;

wherein the micro nozzle is accommodated and attached to the carrier member such that the outlet orifice is aligned with the through-hole, and wherein the carrier member comprises vent holes formed to allow air to flow between the second surface and the first surface.

2. A carrier assembly according to claim 1, wherein the carrier member is formed out of thin sheet metal.

3. A carrier assembly according to claim 2, wherein the vent holes are arranged around the through-hole.

4. A carrier assembly according to claim 2, wherein diameters of the vent holes are between 0.05 mm and 0.3 mm.

5. A carrier assembly according to claim 1, wherein the through-hole of the carrier member is configured to accommodate the micro nozzle such that the outlet surface of the micro nozzle is flush with the first surface, or raised relative to the first surface, of the carrier member when the micro nozzle is accommodated in the through-hole.

6. A carrier assembly according to claim 5, wherein the inlet surface generally parallel with the outlet surface, and a side surface profile connects the outlet surface with the inlet surface, and wherein the side surface profile is configured to cooperate with the through-hole such that the outlet surface is flush with the first surface, or raised relative to the first surface, when the micro nozzle is accommodated in the through-hole.

7. A carrier assembly according to claim 6, wherein the side surface profile cooperates with the through-hole by abutment with an inside surface profile of the through-hole such that the outlet surface is flush with the first surface, or raised relative to the first surface, when the micro nozzle is accommodated in the through-hole.

8. A carrier assembly according to claim 7, wherein the side surface profile of the micro nozzle is angled relative to the outlet surface and wherein the inside surface profile of the through-hole of the carrier member is correspondingly angled relative to the first surface to provide a firm accommodation of the micro nozzle in the through hole.

9. A carrier assembly according to claim 8, wherein the inside surface profile of the through-hole is an angled surface formed by punching a hole from the second surface to the first surface.

10. A carrier assembly according to claim 6, wherein the side surface profile of the micro nozzle is stepped, and wherein the stepped side surface profile of the micro nozzle provides an intermediate, proximally-facing surface between the inlet surface and the outlet surface.

11. A carrier assembly according to claim 10, wherein the intermediate surface of the micro nozzle abuts a distally-facing surface of the inside surface profile of the through-hole, when the micro nozzle is accommodated in the through-hole.

12. A carrier assembly according to claim 1, wherein the micro nozzle comprises a ceramic or a monocrystalline material.

13. A spray device comprising the carrier assembly according to claim 1.

14. A carrier assembly for a spray device, which carrier assembly comprises
   a carrier member adapted to be mounted in a cartridge adapter of a spray device, which carrier member has a proximally directed first surface, a distally directed second surface, and a through-hole placing the first surface in fluid communication with the second surface;
   a micro nozzle having an outlet surface, an inlet surface, and a channel placing an inlet orifice at the inlet surface in communication with an outlet orifice at the outlet surface;
   wherein the micro nozzle is accommodated and attached to the carrier member such that the outlet orifice is aligned with the through-hole, and wherein the carrier member comprises vent holes positioned radially around the through-hole and configured to allow air to flow between the second surface and the first surface,
   wherein the through-hole of the carrier member is configured to accommodate the micro nozzle such that the outlet surface of the micro nozzle is flush with the first surface or in a raised position relative to the first surface of the carrier member.

15. The carrier assembly of claim 14, wherein an inside surface profile of the through-hole is an angled surface.

16. The carrier assembly of claim 15, wherein an intermediate surface of the micro nozzle abuts a distally facing surface of the inside surface profile of the through-hole, when the micro nozzle is accommodated in the through-hole.

17. The carrier assembly of claim 15, the angled surface is formed by punching a hole from the second surface to the first surface.

18. An assembly for a spray device comprising:
   a mouthpiece;
   a cartridge adapter attached to the mouthpiece;
   a carrier member fixedly attached to a proximal end of the cartridge adapter, where the carrier member has a through-hole, and wherein the carrier member further comprises vent holes arranged around the through-hole; and
   a micro nozzle positioned on a distal side of the carrier member and aligned with the through-hole such that an orifice in the micro nozzle allows passage of fluid from the distal side of the carrier member and into the mouthpiece.

* * * * *